United States Patent [19]

Bauer, III et al.

[11] Patent Number: 4,560,650

[45] Date of Patent: Dec. 24, 1985

[54] METHOD AND COMPOSITIONS FOR DETERMINATION OF GAMMA GLUTAMYL TRANSPEPTIDASE

[75] Inventors: Henry W. Bauer, III, Miami; Ravindra S. Shukla, Pembroke Pines, both of Fla.

[73] Assignee: Coulter Electronics, Inc., Hialeah, Fla.

[21] Appl. No.: 502,282

[22] Filed: Jun. 8, 1983

[51] Int. Cl.[4] .................. C12Q 1/48; C12Q 1/36; C12N 9/96

[52] U.S. Cl. .................................. 435/15; 435/24; 435/188; 435/810

[58] Field of Search ............... 435/4, 15, 16, 24, 188, 435/810

[56] References Cited

U.S. PATENT DOCUMENTS

| | | | |
|---|---|---|---|
| 3,703,441 | 11/1972 | Nakanishi et al. | 435/24 |
| 3,892,631 | 7/1975 | Carroll | 435/24 |
| 3,986,931 | 10/1976 | Bernt et al. | 435/4 |
| 4,087,331 | 5/1978 | Bucolo et al. | 435/15 |
| 4,372,874 | 2/1983 | Modrovich | 435/15 |

FOREIGN PATENT DOCUMENTS 18628  11/1980  European Pat. Off. ............. 435/15

OTHER PUBLICATIONS

Rosalki et al., Clin. Chem., 20(9): 1121–1124 (1974).

*Primary Examiner*—Esther M. Kepplinger
*Attorney, Agent, or Firm*—Silverman, Cass & Singer

[57] ABSTRACT

A two-reagent assay system for determination of gamma glutamyl transpeptidase enzyme activity in a biological fluid. Gamma glutamyl-p-nitroanalide substrate for the enzymatic reaction is provided in a first reagent which is a dry mixture of the substrate with a normally solid acid which is water soluble and a second reagent includes a buffer and a component selected for reception of the glutamyl product of the enzymatic reaction.

21 Claims, No Drawings

METHOD AND COMPOSITIONS FOR DETERMINATION OF GAMMA GLUTAMYL TRANSPEPTIDASE

BACKGROUND OF THE INVENTION

This invention relates to the quantitative determination of gamma glutamyl transpeptidase enzyme in biological fluids, particularly human blood serum, and to compositions employed in such assay.

The gamma glutamyl transpeptidase enzyme is present in various biological tissues, such as human and animal kidneys, as well as in urine and blood serum. Elevated levels of gamma glutamyl transpeptidase activity in serum is an indication of liver diseases, and extremely high levels have been associated with cancer of the liver, bile duct obstructions, and heart disorders of postmyocardial infarction. Thus, clinical determination of gamma glutamyl transpeptidase activity in serum has become a routine test in a large volume of pathological diagnosis. In the most widely employed method for determination of gamma glutamyl transpeptidase activity, the enzymatic conversion of the substrate gamma glutamyl-p-nitroanilide (GGpN) is employed. The liberated reaction product, p-nitroaniline, is a yellow-colored compound whose rate of formation is determined optically as the measure of the gamma glutamyl transpeptidase (GGTP) activity. The well known reaction

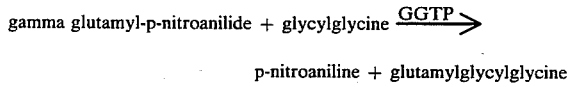

gamma glutamyl-p-nitroanilide + glycylglycine $\xrightarrow{GGTP}$ p-nitroaniline + glutamylglycylglycine was adapted to a clinical procedure for measurement of GGTP activity in serum by Szasz, Clinical Chemistry, 15,124 (1969) and optimized by the Scandinavian Society for Clinical Chemistry and Clinical Physiology, Scand. J. Clin. Lab. Invest., 36, 119 (1976). This method also has been adopted by the American Association for Clinical Chemistry.

One of the disadvantages of this standard procedure is the instability and poor aqueous solubility of the gamma glutamyl-p-nitroanilide substrate. Preparation of a reagent for the procedure encounters difficulty in dissolving the substrate which must be mixed with warm water and heated for five minutes at 50°-60° C. in a water bath or incubator. The reagent must then be cooled at room temperature to 37° C. and used within one hour of cooling at 37° C. in order to prevent precipitation. If precipitation occurs, the reagent must be reheated to 50° C. and again cooled to 37° C. for use. Consequently, it has been necessary to prepare solutions only large enough to perform relatively few determinations as soon as possible. Even with heating, the prepared substrate concentration can only be approximately 3 to 4 mmole/liter.

In the effort to avoid the poor solubility of the GGpN substrate, Rosalki and Tarlow dissolved the substrate in a dilute solution of HCl with limited stability (Clin. Chem., 20, 9 pp. 1121-1124 (1974). To eliminate the inconvenience required in using the HCl reagent, acidic and sulfonic derivatives of the substrate have been developed as described in U.S. Pat. Nos. 3,986,931 and 4,087,331, respectively. While these derivative substrates have improved aqueous solubility, their expense, slower rate of decomposition and multiplied reagent requirements have limited their clinical use. Consequently, GGpN has remained the substrate of choice for GGTP assay.

U.S. Pat. No. 3,878,048 describes the use of surfactants to solublize the GGpN substrate in basic media and once the substrate has been dissolved, the pH is adjusted to approximately 8.2 with addition of hydrochloric acid solution to promote the enzymatic reaction. Subsequent dye-coupling of the -p-nitroaniline reaction product is initiated under acidic condition, and the diazotized product is then optically measured for indication of the GGTP activity of the sample.

Prior art teaches use of a single, dry reagent which comprises GGpN substrate in a tablet or powder and the conventional glycylglycine acceptor for the liberated glutamyl, tris(hydroxymethyl)aminomethane and succinic acid to adjust the pH of the Tris-buffered reconstituted reagent to approximately 8.2. However, reconstitution of the single, dry reagent into the basic pH solution still requires dissolving in warm water at 37° C. in order to form a stable solution. The resulting reagent solution is stable at room temperature for approximately 8 hours but cannot be refrigerated due to precipitation of the substrate.

SUMMARY OF THE INVENTION

The invention provides a new dry mixture comprised of gamma glutamyl-p-nitroanilide substrate (GGpN) with a water soluble, normally solid acid. This dry mixture conveniently can be supplied and stored in solid or powder form. The solid acid is of sufficient acidity to solubilize the substrate in aqueous solution using water at room temperature and without heating. The resulting substrate solution is stable against precipitation under refrigeration at temperatures as low as range 2° to 15° C. for periods as long as one week.

The substrate solution embodying the invention can be employed for assay of GGTP enzyme in biological fluids, both when it is refrigerated as would be required where used in the DACOS ™ Chemical Analyzer manufactured by Coulter Electronics, Inc. of Hialeah, Fla., or non-refrigerated appropriate for other usages.

The invention also provides a new and improved reagent combination for use in determination of GGTP enzyme activity in a biological fluid. The combination includes a first reagent which comprises the dry mixture of GGpN substrate and normally solid acid which can be conveniently reconstituted with water at room temperature to provide an aqueous substrate solution and a second reagent which comprises a buffer and a component for reception of the glutamyl product of the enzymatic reaction. The second reagent is mixed with a solution of the first reagent in order to raise the pH of the combined reagent solutions for promotion of the desired enzymatic reaction which is proportional to the content of the GGTP enzyme in the biological fluid.

DESCRIPTION OF THE PREFERRED EMBODIMENTS

Broadly, according to this invention, the problem of insolubility in water of gamma glutamyl-p-nitroanilide at room temperature in concentration sufficient for gamma glutamyl transpeptidase assay has been solved by separating the GGpN substrate from the other conventional reagent components and mixing it with a solid acid of sufficient acidity to solubilize the substrate without heating. The dry mixture is readily soluble in water at room temperature and the resulting substrate solution is stable against precipitation at room temperature for as long as 24 hours and stable under refrigeration at temperatures as low as the range 2°–15° C. for periods as long as one week.

The refrigeration stability of the substrate solution allows temporary laboratory storage, and use of the reagent in a chemical analyzer such as Coulter Electronics' DACOS ™ instrument which employs refrigerated reagent storage at approximately 15° C.

A second reagent in accordance with this invention for assay of GGTP in biological fluids includes glycylglycine or an equivalent glutamyl acceptor and a buffer such as Tris Base, tris(hydroxymethyl) aminomethane, which maintains the enzymatic reaction solution in the suitable pH range approximately 7.6–8.4, preferably 7.8–8.2, for assay of GGTP activity. Admixing the acidic substrate solution and the buffered glycylglycine solution, with addition of saline diluent, produces a solution with optimal parameters for colorometrically monitoring the GGTP activity in the added biological sample by measurement of the optical absorbance using a wavelength in the range 405–420 nanometer (nm).

Solubilization of the GGpN substrate in aqueous solution at room temperature (20°–25° C.) requires that the dry substrate reagent contain a solid acid of high acidity, generally indicated by $pK_A$ less than 3.0, in order to stabilize a concentration of GGpN in the range approximately 3 to 15 mmol/liter, suitable for subsequent use in enzymatic conversion to determine GGTP activity.

The GGpN substrate is an amphoteric compound and can form a stable salt when heated in basic solution as employed in the conventional procedures for assay of GGTP activity. In accordance with this invention the solid acids having $pK_A$ less than 3.0 are capable of solubilizing the GGpN substrate in water at normal room temperature. Thus, the dry mixture of GGpN substrate and solid acid can be conveniently supplied to and stored in the laboratory as a dry, powdered reagent with very long shelf life of 2 years or longer under refrigeration at approximately 4° C., and the reconstituted substrate reagent solution can be prepared with water at room temperature and without any heating. The reagent solution can then be temporarily stored without precipitation under refrigeration, preferably in the temperature range as low as 2°–15° C.

Suitable solid acids for dry mixture with the GGpN substrate are characterized by high acidity and aqueous ionization, and consequently have low $pK_A$ values less than 3.0. The $pK_A$ is the negative value of the logarithm of the standard aqueous ionization constant $K_A$ at 25° C.:

$$K_A = \frac{[H_3O^+][A^-]}{[HA]}$$

The following table lists representative solid acids suitable for solubilizing the GGpN substrate in accordance with the invention, and indicates the corresponding standard $pK_A$ values of the acids.

TABLE 1

| Solid Acid | Acidity - $pK_A$ |
|---|---|
| Sulfamic | 0.99 |
| Oxalic | 1.27 |
| Maleic | 1.94 |
| Cacodylic | 1.56 |
| Chlorophthalic | 1.60 |

TABLE 1-continued

| Solid Acid | Acidity - $pK_A$ |
|---|---|
| Malonic | 2.86 |

In characterizing suitable solid acids for use in the dry substrate mixture, the acidity and not the chemical identity of the acids is determinative, and both organic and inorganic acids can be employed without adverse effect on the enzymatic reaction for the assay of GGTP. Thus, solid inorganic acids such as sulfamic acid having $pK_A$ of 0.99 and solid organic acids such as chlorophthalic acid having $pK_A$ of 1.60 can solublize GGpN in water at room temperature. Monocarboxylic acids such as cacodylic acid having a $pK_A$ of 1.56 and polycarboxylic acids such as the dicarboxylic acids, oxalic acid, maleic acid, and malonic acid having $pK_A$ of 1.27, 1.94 and 2.86 respectively, can also be employed as the solid acid. Cacodylic acid and oxalic acid are not preferred because of their toxicity and maleic acid is hygroscopic and can tend to form caking as a powder. Sulfamic acid is a preferred solid acid for dry mixture with the GGpN substrate because it will solubilize relatively high concentrations of GGpN, for example in the range of 10 to 20 mmol/liter in water at room temperature. Suitable molar ratio of sulfamic acid to GGpN in the dry mixture can be in the range 2–8:1, preferably about 5–6:1, for optimal aqueous substrate concentration in the range 10 to 15 mmol/liter, preferably 13 mmol/liter, and subsequent dilution with the buffer solution to preferably 5–9 mmole/liter in the initial enzymatic reaction solution.

The substrate solution can be prepared by dissolving the GGpN with the solid acid in deionized water at room temperature to form an aqueous solution having pH in the range 1.2 to 2.2. No heating is necessary to dissolve the dry mixture, and the substrate solution is ready for use or can be stored under refrigeration without precipitation at temperature in the range 2°–15° C.

In the preferred composition, a dry mixture of GGpN and the solid acid further includes sodium chloride which provides added stability to the aqueous substrate reagent prepared from the dry mixture. In the dry mixture, suitable molar ratio of the solid acid and GGpN substrate will be in the range 2–20:1, preferably 5–15:1, for assay of the GGTP enzyme in biological fluid.

In the preferred assay procedure, the sample of the fluid containing the GGTP enzyme to be assayed is diluted with normal saline and added to the buffer solution containing the glutamyl receptor component. Thereafter, the resulting solution is combined with the acidic substrate solution to produce a final pH of the reaction solution preferably in the range 7.6–8.4 for optimal activity of the GGTP enzyme. The preferred buffer in the buffer reagent is tris(hydroxymethyl) aminomethane. Other suitable buffers may be employed, such as tris(hydroxymethyl)-aminomethane hydrochloride, Ammediol hydrochloride (2-amino-2-methylpropane-1, 3-diol hydrochloride), and phosphate buffers.

The preferred glutamyl receptor contained in the buffer reagent is glycylglycine. Other suitable glutamyl receptors include asparagine, methionine, L-phenylalanine, and hydroxylamine.

Table 2 presents a preferred composition for the aqueous substrate solution indicating the components and proportions per liter of solution. Table 3 presents a preferred composition for the aqueous buffer solution indicating the components and proportions per liter of solution.

TABLE 2

| Component | Proportion |
| --- | --- |
| Sulfamic Acid | 75 mmole |
| Gamma-Glutamyl-p-Nitroanilide | 13 mmole |
| NaCl | 213 mmole |

TABLE 3

| Component | Proportion |
| --- | --- |
| Tris(hydroxymethyl) Aminomethane | 450 mmole |
| Glycylglycine | 600 mmole |

The buffered reaction solution, at a preferred pH of about 7.8, is incubated at a preferred temperature of 37° C. for optimal activity of the GGTP enzyme. The reaction progress is monitored by measuring absorbance at the preferred wavelength of 420 nm in a spectrophotometer such as provided in the DACOS TM automatic analyzer. The absorbance change at 420 nm corresponds to the amount of p-nitroaniline released during the enzymatic reaction, and indicates the activity of GGTP enzyme. The concentration of p-nitroaniline can be determined by comparison against a standard curve prepared from absorbancies of aqueous solutions containing various concentrations of free p-nitroaniline. Direct conversion from absorbance at 37° C. to concentration of GGTP can be made according to the following:

$$U/L = OD/\text{minute} \times 5125$$

Where:
U/L is the expressed activity of GGTP in International Units defined as that amount of enzyme activity which promotes the conversion of GGpN to p-nitroaniline at the rate of one micromole per minute at the prescribed assay condition;
OD is the change in optical density; and
5125 is a factor including the extinction coefficient at 420 nm, reaction solution volume, and light path of 1 cm. The dynamic range of the described procedure results in the indicated linearity up to 1,300 U/L of GGTP.

The following examples are illustrative of the reagents and procedure in accordance with this invention, but do not indicate limitation upon the scope of the claims. The room temperature was 24° C.

EXAMPLE 1

Buffer Reagent

To 250 ml of distilled water at room temperature, 18.73 gm of tris(hydroxymethyl)aminomethane and 27.25 gm of glycylglcine were added with stirring and were completely dissolved in less than 3 minutes resulting in a solution at pH 8.20.

Substrate Reagent

To 625 ml of distilled water at room temperature, 4.551 gm of sulfamic acid and 2.173 gm of gamma glutamyl-p-nitroanilide were added with stirring. The resulting solution was clear.

Enzymatic Reaction

To 0.8 ml of the buffer solution, 0.4 ml of saline (0.9% W/V sodium chloride in water) and 0.08 ml of blood serum sample were added. Then, 2.0 ml of the substrate solution were added, and the resulting reaction solution at pH 7.8 was incubated at 37° C. The reaction progress was monitored at a wavelength of 420 nm.

EXAMPLE 2

Determination of the blood serum assay in a DACOS TM Analyzer was carried out as follows:

To 40 uL of saline were added 80 ul of buffer solution from Example 1 and 8 ul of serum sample. Then 200 ul of substrate solution from Example 1 were added. The buffer solution and the substrate solution had been refrigerated at 15° C., and the combined reaction solution was incubated at 37° C. The reaction was monitored at 420 nm and the enzyme concentration was calculated using the the following correlation for GGTP activity; $U/L = OD/\text{minute} \times 5125$.

EXAMPLE 3

Buffer Reagent

To 80 ml of distilled water at room temperature, 10.80 gm of tris(hydroxymethyl)aminomethane and 8.72 gm of glycylglcine were added with stirring and were completely dissolved in less than 3 minutes resulting in a solution at pH 8.1.

Substrate Reagent

To 200 ml of distilled water at room temperature, 300 gm of oxalic acid and 0.070 gm of gamma glutamyl-p-nitroanilide were added with stirring. The resulting solution was clear in less than 5 minutes without heating, and had a pH of 1.38.

Enzymatic Reaction

To 0.8 ml of the buffer solution, 0.4 ml of saline (0.9% W/V sodium chloride in water) and 0.08 ml of blood serum sample were added. Then, 2.0 ml of the substrate solution were added, and the resulting reaction solution at pH 7.79 was incubated at 37° C. The reaction progress was monitored at a wavelength of 420 nm.

EXAMPLE 4

Buffer Reagent

To 80 ml of distilled water at room temperature, 14.12 gm of tris(hydroxymethyl)aminomethane and 8.72 gm of glycylglcine were added with stirring and were completely dissolved in less than 3 minutes resulting in a solution at pH 8.1.

Substrate Reagent

To 200 ml of distilled water at room temperature, 43.0 gm of maleic acid and 0.070 gm of gamma glutamyl-p-nitroanilide were added with stirring. The resulting solution was clear in less than 5 minutes without heating, and had a pH of 1.47.

Enzymatic Reaction

To 0.8 ml of the buffer solution, 0.4 ml of saline (0.9% W/V sodium chloride in water) and 0.08 ml of blood serum sample were added. Then, 2.0 ml of the substrate solution were added, and the resulting reaction solution at pH 7.7 was incubated at 37° C. The reaction progress was monitored at a wavelength of 420 nm.

EXAMPLE 5

Buffer Reagent

To 8 ml of distilled water at room temperature, 2.86 gm of tris(hydroxymethyl)aminomethane and 0.872 gm of glycylglycine were added with stirring and were completely dissolved in less than 3 minutes resulting in a solution at pH 8.7.

Substrate Reagent

To 20 ml of distilled water at room temperature, 800 mg of malonic acid and 70.0 mg of gamma glutamyl-p-nitroanilide were added with stirring. The resulting solution was clear in less than 5 minutes without heating, and had a pH of 1.55.

Enzymatic Reaction

To 0.8 ml of the buffer solution, 0.4 ml of saline (0.9% W/V sodium chloride in water) and 0.08 ml of blood serum sample were added. Then, 2.0 ml of the substrate solution were added, and the resulting reaction solution at pH 7.53 was incubated at 37° C. The reaction progress was monitored at a wavelength of 420 nm.

When prepared using the solid acid as stabilizer, the substrate reagent has the following advantages:

1. the substrate concentration can be fully optimized for use at 37°;
2. the substrate dissolves very quickly without any inconvenient manipulations by the user, such as heating;
3. the reagent does not require special solvents, such as HCl or organic liquids;
4. the reagent can be refrigerated without precipitation.

We claim:

1. A diagnostic composition for determination of gamma glutamyl transpeptidase enzyme activity in biological fluids, comprising:
   A. gamma glutamyl-p-nitroanilide; and
   B. a water soluble, normally solid acid comprising sulfamic acid in an amount sufficient to provide sufficient acidity to solubilize said composition in water at room temperature for preparation of an aqueous substrate reagent.

2. The composition as claimed in claim 1 wherein said composition comprises an aqueous solution at a gamma glutamyl-p-nitroanilide concentration in the range 2 to 15 mmole/liter.

3. The composition as claimed in claim 2 wherein said solution has a temperature in the range 2°–15° C., without precipitation.

4. The composition as claimed in claim 3 wherein said concentration is within the range 10 to 15 mmole/liter.

5. The composition as claimed in claim 4 wherein said temperature is in the range of 2°–8° C.

6. The composition as claimed in claim 1 wherein said acid further comprises at least one component selected from the group consisting of oxalic acid, maleic acid and malonic acid.

7. The composition as claimed in claim 1 wherein said composition is a dry mixture of said components.

8. The composition as claimed in claim 1 wherein said composition comprises an aqueous solution of said components having pH in the range 1.2 to 2.2.

9. The composition as claimed in claim 1 wherein said composition is an aqueous solution comprising said components.

10. The composition as claimed in claim 9 wherein said solution is buffered to maintain a pH in a range 7.6 to 8.4.

11. The composition as claimed in claim 10 wherein said solution is buffered with tris(hydroxymethyl)aminomethane.

12. The composition as claimed in claim 1 wherein the molar concentration ratio of said acid to said gamma glutamyl-p-nitroanilide is in the range 2 to 20:1.

13. A two-reagant assay system for determination of gamma glutamyl transpeptidase enzyme activity in biological fluids, which system comprises a first dry reagent comprising gamma glutamyl-p-nitroanilide and sulfamic acid in an amount sufficient to dissolve said first reagent in water at room temperature to provide a stable aqueous substrate solution, and a second reagent comprising a glutamyl receptor and a buffer, for admixture with a solution of said first reagent in order to raise the pH of said combined reagents for promotion of enzymatic reaction proportional to the content of said gamma glutamyl transpeptidase in said fluid.

14. The assay system as claimed in claim 13 wherein said first reagent comprises said acid and said gamma glutamyl-p-nitroanilide in molar ratio thereof within the range 2–20:1.

15. The assay system as claimed in claim 13 wherein said first reagent comprises a composition comprising the following components and relative proportions;

| Component | Proportion |
| --- | --- |
| Sulfamic Acid | 2–8 mmoles |
| Gamma Glutamyl-p-Nitroanilide | 1 mmole |

16. The assay system as claimed in claim 13 wherein said first reagent further comprises sodium chloride.

17. The assay system as claimed in claim 13 wherein said second reagent is a dry composition.

18. The assay system as claimed in claim 13 wherein said first reagent comprises an aqueous solution of the following components and the proportions indicated per liter of solution:

| Component | Proportion |
| --- | --- |
| Sulfamic Acid | 75 mmole |
| Gamma Glutamyl-p-Nitroanilide | 13 mmole |
| NaCl | 213 mmole | and said second reagent comprises an aqueous solution of the following components in the proportions indicated per liter of solution:

| Component | Proportion |
| --- | --- |
| Tris(hydroxymethyl) Aminomethane | 450 mmole |
| Glycylglycine | 600 mmole |

19. A method for determination of gamma glutamyl transpeptidase enzyme activity in a biological fluid, comprising:
   A. dissolving in water at room temperature a dry composition comprising a mixture of gamma glutamyl-p-nitroanilide and sulfonic acid in an amount sufficient to completely solubilize said composition in said water, to prepare an aqueous solution having a pH in the range 1.2 to 2.2;
   B. raising the pH of said solution to basic condition; and
   C. reacting said basic solution with said biological fluid containing said gamma glutamyl transpeptidase enzyme in order to monitor the enzymatic activity thereof.

20. The method of claim 19, further comprising cooling the acidic solution from step A to a temperature in the range 2°–15° C. without precipitation, prior to step B.

21. A method for determination of gamma glutamyl transpeptidase enzyme activity in a biological fluid, comprising:

A. preparing a composition comprising a dry mixture of gamma glutamyl-p-nitroanilide and sulfonic acid in an amount sufficient to completely solubilize said composition in water at room temperature;

B. dissolving completely said composition in water at room temperature to prepare an aqueous solution thereof having a pH in the range 1.2 to 2.2;

C. raising the pH of said solution to basic condition; and

D. reacting said basic solution with said biological fluid containing said gamma glutamyl transpeptidase enzyme in order to monitor the enzymatic activity thereof.

* * * * *